Figure 1:
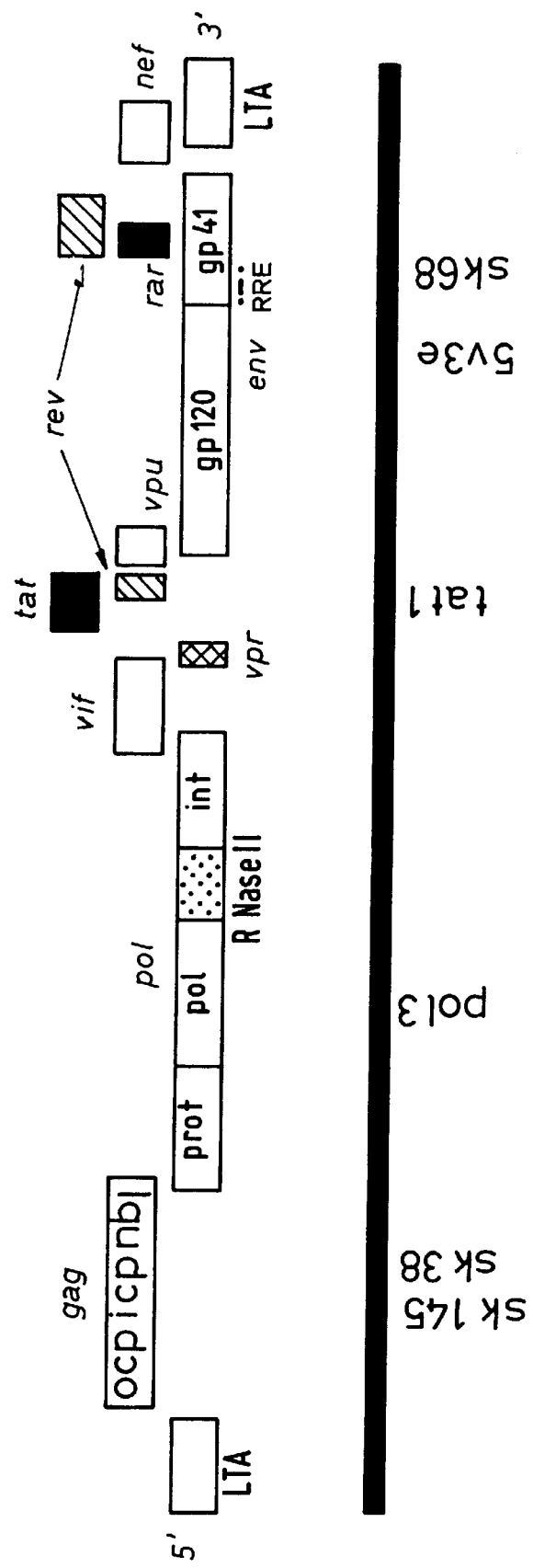

United States Patent [19]
Hauser et al.

[11] Patent Number: 6,162,631
[45] Date of Patent: *Dec. 19, 2000

[54] RETROVIRUS FROM THE HIV GROUP AND ITS USE (MVP-2901/94)

[75] Inventors: Hans-Peter Hauser; Stefan Knapp; Stefan Brust, all of Marburg; Lutz G. Gürtler, Munich; Josef Eberle, Freising; Lazare Kaptue; Léopold Achengui Zekeng, both of Yaoundé/Cameroun, all of Germany

[73] Assignee: Behringwerke Aktiengesellschaft, Marburg, Germany

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/989,493

[22] Filed: Dec. 12, 1997

Related U.S. Application Data

[63] Continuation of application No. 08/602,713, Feb. 16, 1996, Pat. No. 5,798,205.

[30] Foreign Application Priority Data

Feb. 16, 1995 [DE] Germany ............................ 195 05 262

[51] Int. Cl.[7] .................................................. G09B 19/00
[52] U.S. Cl. ........................................ 435/235.1; 439/974
[58] Field of Search ..................... 435/235, 236, 435/239, 235.1, 974; 530/324, 325, 326, 327, 328, 350, 395

[56] References Cited

U.S. PATENT DOCUMENTS

| | | |
|---|---|---|
| 2,107,732 | 10/1938 | Gurtler et al. . |
| 5,759,770 | 6/1998 | Guertler et al. ............................ 435/5 |
| 5,798,205 | 8/1998 | Hauser et al. .............................. 435/5 |

FOREIGN PATENT DOCUMENTS

| | | |
|---|---|---|
| 1353295 | 9/1995 | Australia . |
| 591914 | 10/1995 | European Pat. Off. . |
| 727483 | 9/1997 | European Pat. Off. . |
| 9612809 | 5/1996 | WIPO . |
| 9627013 | 9/1996 | WIPO . |

OTHER PUBLICATIONS

Vanden Haesevelde et al., "Genomic Cloning and Complete Sequence Analysis of a Highly Divergent African Human Immunodeficiency Virus Isolate," *Journal of Virology*, 68:3:1586–1596 (1994).

Charneau et al., "Isolated and Envelope Sequence of a Highly Divergent HIV–1 Isolate: Definition of a New HIV–1 Group," *Journal of Virology*, 205:247–253 (1994).

EMBL Release 42, Cohen et al., Mar. 1995.

*Primary Examiner*—Jeffrey Stucker
*Attorney, Agent, or Firm*—Fulbright & Jaworski, LLP

[57] ABSTRACT

A novel immunodeficiency virus is disclosed which has the designation MVP-2901/94 and which has been deposited with the European Collection of Animal Cell Cultures (ECACC) under No. V 95012601. The characteristic antigens which can be obtained from the virus and which can be employed for detecting antibodies against retroviruses which are associated with immunodeficiency diseases are also disclosed, as are the partial DNA and amino acid sequences of the virus.

6 Claims, 1 Drawing Sheet

RETROVIRUS FROM THE HIV GROUP AND ITS USE (MVP-2901/94)

This application is a continuation of application Ser. No. 08/602,713 filed Feb. 16, 1996, now U.S. Pat. No. 5,798,205.

The present invention relates to a novel retrovirus from the HIV group which is presently designated more precisely as HIV subtype O, and to variants or parts thereof which contain the essential properties of the virus. A process is described for culturing the retrovirus. The invention furthermore relates to the isolation of this retrovirus and to the use of the virus, its parts or extracts for medicinal purposes, for diagnosis and in the preparation of vaccines.

In humans who are infected with them, retroviruses which belong to the so-called HIV group lead to disease symptoms which are summarized under the collective term immunodeficiency or AIDS (acquired immune deficiency syndrome).

Epidemiological studies verify that the human immunodeficiency virus (HIV) is the etiological agent for the overwhelming majority of AIDS (acquired immune deficiency syndrome) cases. A retrovirus which was isolated from a patient and characterized in 1983 was given the designation HIV-1 (Barré-Sinoussi, F. et al., Science 220, 868–871 [1983]). A variant of HIV-1 is described in WO 86/02383.

A second group of human immunodeficiency viruses was identified in West Africa in 1985 (Clavel, F. et al., Science 233, 343–345 [1986]) and designated human immunodeficiency virus type 2 (HIV-2) (EP-A 0 239 425). HIV-2 retroviruses clearly differ from HIV-1 but are also related to monkey immunodeficiency viruses (SIV-2). Like HIV-1, HIV-2 also gives rise to an AIDS symptomatology.

New HI viruses, as represented by ANT70 (J. Vir., 1994, Vol. 68, No. 3, pp. 1586–1596) and MVP-5180/91 (J. Vir., 1994, Vol. 68, No. 3, pp. 1581–1585) have recently been described which can not be classified in HIV-1 subtypes A–F. Owing to their clear structural differences from the known HIV-1 strains, both isolates have provisionally been classified together under subtype O (G. Myers, Los Alamos Data Base), although they clearly differ from each other in their genomic nucleotide sequences.

It is a characteristic of human immunodeficiency viruses that they exhibit a high degree of variability which markedly complicates the comparability of the different isolates. When different HIV-1 isolates are compared, high degrees of variability are found, for example, in some regions of the genome whereas other genome regions are comparatively well conserved (Benn, S. et al., Science 230, 949–951 [1985]). HIV-2 has also been reported to exhibit a very high degree of polymorphism (Clavel, F. et. al., Nature 324, 691–695 [1986]). Regions in the gag and pol genes which encode proteins which are structurally and enzymatically essential possess the greatest genetic stability. By contrast, some regions in the env gene, and also the genes (vif, vpr, tat, rev. nef) which encode regulatory proteins, exhibit a high degree of variability.

It was furthermore demonstrated that antisera against HIV-1 also cross-react with HIV-2 gag and pol gene products even though only low sequence homologies were present. The hybridization between these two viruses was likewise of no great significance unless conditions of very low stringency were used (Clavel, F. et al., Nature 342, 691–695 [1986]).

Due to the wide distribution of the retroviruses from the HIV group, and to the fact that a period of from a few to many years (2–20) elapses between the time of infection and the time at which definite symptoms of pathological changes are recognizable, it is epidemiologically of great importance to ascertain infection with retroviruses of the HIV group at as early a stage as possible and, in particular, in a reliable manner. This is of importance not only in the diagnosis of patients who are exhibiting signs of immunodeficiency, but, even more so, in the screening of blood donors. It has emerged that when retroviruses, or components thereof, of the HIV-1 or HIV-2 type are used in detection systems, antibodies either cannot be detected or can be detected only weakly in some sera, even though signs of immunodeficiency occur in the patients from whom the sera are derived. In certain cases, such detection is possible using the HIV group retrovirus according to the invention.

The genotypic diversity of the HIV viruses presents a substantial problem for diagnosis in particular. In the case of the HIV-1 viruses, it is assumed that one nucleotide is changed per genome in each replication cycle. As a result of this genetic variability, the HIV viruses are able to respond in an extraordinarily flexible manner to the in-vivo selection pressure and to generate, extremely rapidly, mutants which either are resistant to pharmacological agents or are able to attack individuals who have built up a certain degree of immunological protection (Sharp et al., "Origins and diversity of human immunodeficiency viruses", AIDS 1994, vol. 8, Suppl. 1; S 27–S 42).

In order to prevent the spread of infections, in particular in association with blood transfusions but also in association with organ donations, it should be possible to ascertain an infection with an HIV virus with, if possible, 100% certainty. For this reason, it is also necessary diagnostically to detect those infections which are caused by a virus which, while currently only being distributed in certain geographical regions, is able without difficulty—unless suitable preventive measures are taken—to spread into Europe or the United States of America.

A description is given of the isolation and characterization of a novel human immunodeficiency virus, designated MVP-2901/94 hereinafter, which was isolated in 1994 from the peripheral lymphocytes of a 24 year old female patient from the Cameroons who was exhibiting signs of immunodeficiency. From the point of view of geography, this retrovirus originates from a region in Africa which is located between West Africa, where infection with HIV-2 and HIV-1 viruses is endemic, and East Africa, where it is almost exclusively HIV-1 which is disseminated. Consequently, the present invention relates to a novel retrovirus of the HIV subtype O group, which retrovirus is designated MVP-2901/94, and to its variants, to DNA sequences, amino acid sequences and constituent sequences derived therefrom, and to test kits containing the latter.

MVP-2901/94 can be propagated in the MT2 and Jurkat cell lines. The isolation and propagation of viruses are described in detail in the book "Viral Quantitation in HIV Infection, Editor Jean-Marie Andrieu, John Libbey Eurotext, 1991". The procedural methods described therein are incorporated in the disclosure of the present application by reference.

In order to provide a better understanding of the differences between the MVP-2901/94 virus according to the invention and the HIV-1 and HIV-2 retroviruses, the structure of the retroviruses which cause immunodeficiency will first of all be explained briefly. In the centre of the virus, the RNA is located in a conical core which is assembled from protein subunits which carry the designation p 24 (p for protein). This inner core is surrounded by a protein coat which is constructed from protein p 17 (outer core), and by a glycoprotein coat which, in addition to lipids, which originate from the host cell, contains the transmembrane protein gp 41 and the coat protein 120 (gp 120). This gp 120 then binds to the CD-4 receptors of the host cells.

As far as is known, the RNA of the HIV viruses—portrayed in a simplified manner—possesses the following gene regions: so-called long terminal repeats (LTR) at each end, together with the following gene regions: gag, pol, env and nef. The gag gene encodes, inter alia, the core proteins, p 24 and p 17, the pol gene encodes the reverse transcriptase, the protease, the RNAse H and the integrase, and the env gene encodes the glycoproteins, gp 41 and gp 120, of the virus coat. The nef gene encodes a protein having a regulatory function. The arrangement of the genome of retroviruses of the HIV type is shown diagrammatically in FIG. 1.

The so-called PCR (polymerase chain reaction) has become a genetic manipulation method which has a multiplicity of possible uses, and the components which are required for implementing the method can be purchased. Using this method, it is possible to amplify DNA sequences if DNA regions of the sequence to be amplified are known. Short, complementary DNA fragments (oligonucleotides= primers) which anneal to a short region of the nucleic acid sequence to be amplified have then to be synthesized. For carrying out the test, HIV nucleic acids are introduced together with the primers into a reaction mixture which additionally contains a polymerase and nucleotide triphosphates. The polymerization (DNA synthesis) is carried out for a defined time, and the nucleic acid strands are then separated by heating. After cooling, the polymerization then proceeds once more. If, therefore, the retrovirus according to the invention is an HIV-1 or HIV-2 virus, it should be possible to amplify the nucleic acid using primers which are conserved within the known sequences of the HIV-1 and HIV-2 viruses. Some primers of this type have previously been described (Laure, F. et al., Lancet ii, (1988) 538–541 for pol 3 and pol 4, and ou C. Y. et al., Science 239 (1988) 295–297 for sk 38/39, sk 68/69).

However, these primers are not able to amplify DNA from the MVP-5180/91 HIV isolate (J. Vir. 1994, vol. 68, no. 3, pp. 1581–1585). Use of these primers likewise failed to amplify DNA from the MVP-2901/94 isolate, supporting the view that this isolate also diverges strongly from the HIV-1 consensus sequence. It was necessary, therefore, to construct a wide variety of new primers which were derived from known sequences and which were as strongly conserved as possible, and to use them in as many combinations as possible while varying the reaction conditions. Surprisingly, it was found that it was possible to amplify the DNA of MVP-2901/94, and thus gain a first lead into the sequence of the isolate, using a combination of the primers 212 and 412 which were derived from the sequence of the MVP-5180/91 isolate, under the reaction conditions given in Example 4.

```
        5'                               3'    (Seq. ID No. 1)
    212 AGT GCA GCA GGT AGC ACT ATG

5'                               3'    (Seq. ID No. 2)
    412 GTT CCA TTT TAC TGA TGT GTA
```

Once a constituent region of the sequence of an HI virus has been decoded, as it has in the present case, the entire genome of the virus can be cloned and sequenced using known, standard molecular biological methods.

1) This can, for example, be achieved by cloning a cDNA in the following manner: the virus is precipitated from an appropriately sized culture volume (approximately 1 l) and resuspended in phosphate-buffered sodium chloride solution. It is then pelleted through a (20%) sucrose cushion. The virus pellet can be suspended in 6 M guanidinium chloride in 20 mM dithiothreitol and 0.5% Nonidet P 40. CsCl is added to a concentration of 2 molar, and the solution containing the disrupted virus is loaded onto a cesium chloride cushion. The viral RNA is then pelleted by centrifugation, dissolved, extracted with phenol and precipitated with ethanol and lithium chloride. The synthesis of the first cDNA strand is carried out on the viral RNA, or parts thereof, using an oligo(dT) primer. The synthesis, for which reverse transcriptase is added, can be carried out using a commercially available kit. For the synthesis of the second strand, the RNA strand of the RNA/DNA hybrid is digested with RNase H, and the second strand is synthesized using *E. Coli* DNA polymerase I. Blunt ends can then be produced using T4 polymerase, and these ends can be bonded to suitable linkers for restriction cleavage sites. Following restriction digestion with the appropriate restriction endonuclease, the cDNA fragment is isolated from an agarose gel and ligated to a vector which has previously been cut in a suitable manner. The vector containing the cDNA insert can then be used to transform competent *E. coli* cells. The resulting colonies are then transferred to membranes, lyzed and denatured, and finally detected by hybridization with nucleic acid which is labeled with digoxigenin or biotin. Once the corresponding cDNA has been prepared by genetic manipulation, it is possible to isolate the desired DNA fragments originating from the retrovirus. Incorporation of these fragments into suitable expression vectors then makes it possible for the desired protein or protein fragment to be expressed and employed for the diagnostic tests.

2) As an alternative to the stated method, the nucleic acid of the immunodeficiency virus can be cloned with the aid of PCR technology. To do this, it is necessary in each case to identify, from the still unknown region of the sequence, primers which can, in combination with the primers derived from the known part of the sequence, render it possible to amplify the DNA of the isolate.

3) A further possibility of cloning the virus by proceeding from the known sequence segment is that of cloning the proviral genomic DNA of the virus. For this purpose, genomic DNA from an infected cell line is first purified by standard methods. The proviral DNA, which is integrated into the host genome, can then be cloned after constructing and screening a genomic library. To do this, the genomic DNA is partially fragmented, and the fraction containing fragments of a length of about 10–25 kb is isolated and cloned into a vector system, such as cosmids or lambda phages, which is able to accommodate fragments of this length. Using the selected vector system, the mixture of the genomic fragments is transformed into an *E. coli* strain. Vectors which contain the viral genome can then be identified by hybridization with a cloned DNA fragment of the sought-after virus, which fragment is labeled radioactively or in some other way, and subsequently isolated (plaque screening or colony screening). The viral game is thereby made available for sequence analysis and for expression of its proteins.

The similarity between different virus isolates can be expressed by the degree of homology between the nucleic acid or protein sequences. 50% homology means, for example, that 50 out of 100 nucleotide or amino acid positions in the sequences correspond to each other. The homology of proteins is determined by sequence analysis. Homologous DNA sequences can also be identified by the hybridization technique.

The present invention therefore relates to an immunodeficiency virus of the HIV group, or variants of this virus, which exhibits morphological and immunological properties which correspond to those of the retrovirus which is deposited with the European Collection of Animal Cell Cultures (ECACC) under No. V 95012601 and which has the designation MVP-2901/94. The date of deposition was Jan. 26, 1995.

The essential morphological and immunological properties of the immunodeficiency virus are understood to mean those structures which are of decisive importance for the immunological characterization of the virus. In this context, those epitopes are particularly crucial which give rise to an amplified production of antibodies in infected persons and which are suitable for dividing the viruses into different subclasses and subtypes. Consequently, the epitopes which are of importance in this context are, in particular, not those which are also present in viruses of the HIV-1 and/or HIV-2 groups but rather those epitopes which occur only in the deposited virus according to the invention and in those variants which belong to the narrow group of the MVP-2901/94 virus. The morphological and immunological properties of the virus are also mirrored in the diagnostically relevant region of the coat protein.

The invention also embraces immunodeficiency viruses which exhibit an RNA sequence which possesses at least 75% homology, based on the entire genome, with the RNA of the deposited virus.

Preferred immunodeficiency viruses are those which exhibit an RNA sequence which possesses at least 85%, and particularly preferably at least 90%, homology, based on the entire genome, with the RNA of the deposited virus. Very particularly preferred immunodeficiency viruses are those which possess 92%, or even 95%, homology, based on the entire genome, with the RNA of the deposited virus.

The immunodeficiency viruses according to the invention exhibit an RNA sequence which is complementary to the DNA sequence in Table 1 and possesses at lest 75% homology with this sequence in Table 1. In a preferred form, the immunodeficiency viruses according to the invention exhibit an RNA sequence which is complementary to the DNA sequence in Table 1 and possesses at least 85% homology with the sequence in Table 1. In this context, the homologous moiety of the sequence is at lest 50 nucleotides in length and, in a preferred embodiment, at least 100 nucleotides in length.

The immunodeficiency viruses according to the invention exhibit a sequence or a constituent sequence which is complementary to the sequence depicted in Table 1 or is homologous with this sequence, with the difference from the sequence given in Table 1, based on the diagnostically relevant region, being at most 20% at the nucleotide level and 25% at the protein level.

In a preferred embodiment, the difference from the sequence given in Table 1, based on the diagnostically relevant region, is at most 10% at the nucleotide level and 15% at the protein level.

The present invention also relates to a cDNA which is complementary to the RNA, or parts thereof, of the immunodeficiency virus MVP-2901/94, which is deposited at the European Collection of Animal Cell Cultures (ECACC) under No. V 95012601, or of a virus according to the invention.

In the preferred embodiment, this cDNA is in the form of recombinant DNA.

The invention also embraces antigens which are prepared using the cDNA according to the invention or the recombinant DNA, or using the amino acid structure which can be deduced from its cDNA. In this context, the antigen is a protein or peptide.

In a preferred embodiment, the antigens according to the invention exhibit an amino acid sequence which corresponds to the amino acid sequence depicted in Table 1 or to a constituent sequence thereof.

Preferably, the antigen exhibits a constituent sequence having at least 10 amino acids, particularly preferably having at least 20 amino acids, selected from the amino acid sequence in Table 1.

In a particularly preferred embodiment, the antigen according to the invention exhibits an amino acid sequence NQQLLNLWGCKGKLICYTSVKWN or a constituent sequence thereof having at lest 10 consecutive amino acids.

The present invention also embraces antigens which are prepared from an immunodeficiency virus according to one of claims 1 to 6 and are, for example, in the form of purified viral preparations. The antigen according to the invention is preferably prepared by recombinant means; however, it is also possible to prepare the antigen synthetically, for example by solid phase synthesis.

The invention also embraces test kits for detecting antibodies against viruses which cause immune deficiency, which contain at least one antigen according to the invention.

The test kits can be based on Western blots, ELISA tests or fluorescence antibody detection tests. Recently, it has emerged that those methods in which the viral nucleic acid, or a specific region thereof, is amplified are very sensitive and effective for diagnosing viruses, and in particular HIV viruses.

One of the known detection methods is the polymerase chain reaction (PCR). As an alternative to this, the competitive polymerase chain reaction can also be used for detecting HIV infections (for example AIDS (1993), 7, Suppl. 2; S 65–S 71).

Another detection method, which has recently gained in importance especially in relation to HIV diagnosis, is the NASBA (nucleic acid sequence-based amplification) method. This method is described, for example, in AIDS 1993, 7 (Suppl. 2): S 107–S 110. In this method, the single-stranded RNA, or else the double-stranded DNA, is amplified with T7 RNA polymerase and then detected.

A further method for detecting HIV viruses is that of detection by means of signal amplification using branched DNA. This is described, for example, in AIDS 1993, 7 (Suppl. 2): S 11–S 14. In this method, the viral nucleic acid is hybridized to probes which are bound to a solid phase. Furthermore, a detection molecule (branched DNA structures) is hybridized to the probe and then detected enzymatically.

A feature shared in common by the above methods is that defined nucleic acid regions, which are specific for the virus to be detected, are employed in the detection methods. In the case of these detection methods, defined, short nucleic acid fragments, which are, in particular DNA fragments, are selected and employed in the detection methods.

The present invention also relates, therefore, to those nucleic acid fragments which exhibit a sequence which corresponds to a nucleic acid according to the invention or is complementary to this nucleic acid. These nucleic acid fragments, which can, for example, be primers, have, as a rule, a length of at least 15, preferably at least 25, and particularly preferably at least 35, nucleotides. Thee nucleic acid fragments may be used, in accordance with the invention, in methods for detecting HIV viruses.

The immunodeficiency viruses according to the invention the cDNA according to the invention and the antigens may be used for detecting retroviruses which cause immune deficiency.

The antigens according to the invention, in particular, may be used for preparing vaccines.

The invention also relates to ribonucleic acid which encodes a virus according to the invention.

Within the scope of the present invention, a part of the coat protein was sequenced which is of particular relevance for diagnosis. This part is an envelope region which encompasses the area of the so-called V3 loop; the region which was sequenced within the scope of the present invention extends into the so-called gp 41 region.

Within the scope of the present invention, a part of the coat protein was first sequenced and it was established that this sequence exhibits only a relatively low degree of homology with the corresponding sequences of viruses of the HIV type. Comparison with HIV sequences, which was carried out using databases, indicated that the gp 41 region, in particular, was at most 79.1% homologous at the nucleotide level.

The sequence of the virus according to the invention differs from that of previously known viruses. The present invention relates, therefore, to those viruses, and corresponding DNA and amino acid sequences, which substantially correspond with the sequence of the virus according to the invention, with the degree of deviation being determined by the degree of homology. An homology of, for example, more than 85% denotes, therefore, that those sequences are encompassed in which at least 85 out of 100 nucleotides or amino acids are the same nucleotides or amino acids, while the remainder can be different. When homology is being established, the two sequences are aligned in such a way that the greatest possible number of nucleotides or amino acids which correspond to each other coincide with each other.

On the basis of the isolated sequence, immunodominant epitopes (peptides) can be formulated and synthesized. Since the nucleic acid sequence of the virus is known, the person skilled in the art can deduce the amino acid sequence from this. A constituent region of the amino acid sequence is given in Table 1. The present invention also relates, therefore, to antigens, i.e. proteins, oligopeptides or polypeptides, which can be prepared using the information disclosed in Table 1. These antigens, proteins, polypeptides and oligopeptides exhibit amino acid sequences which are given in Table 1. The antigens or peptides can exhibit relatively short constituent sequences of an amino acid sequence which is reproduced in Table 1. This amino acid sequence is at least 10 amino acids, preferably at least 20, and particularly preferably at least 25, amino acids in length. In addition to using recombinant technology, these peptides can also be prepared by synthetic methods. A suitable route of preparation is solid phase synthesis of the Merrifield type. Further description of this technique, and of other methods which are known from the state of the art, can be found in the literature, for example M. Bodansky, et al., Peptide Synthesis, John Wiley & Sons, 2nd Edition 1976.

In the diagnostic tests, a serum sample from the person to be investigated is brought into contact with the protein chains of one or more proteins or glycoproteins (which can be expressed in eukaryotic cell lines), or parts thereof, which derive from MVP-2901/94. Test methods which are preferred include the immunofluorescence or immunoenzymic test methods (e.g. ELISA and immunoblot).

In the immunoenzymic tests (ELISA), antigen which derives from MVP-2901/94, or a variant thereof, can, for example, be bound to the walls of microtiter plates. The dose which is used in this context essentially depends on the test system and on the treatment of the microtiter plates. Serum, or serum dilutions, which derive from the person to be investigated are then added to the wells of the microtiter plates. After a defined incubation period, the plate is washed and specific immune complexes are detected with antibodies which bind specifically to human immunoglobulins and which have been linked beforehand to an enzyme, for example horseradish peroxidase, alkaline phosphatase, etc., or to an enzyme-labeled antigen. These enzymes can convert a colorless substrate into a highly colored product, and the presence of specific anti-HIV antibodies can then be determined from the intensity of the color. Another possible use for the virus according to the invention in test systems is its use in Western blots.

Even though it is proving extremely difficult to prepare vaccines against immunodeficiency diseases, this virus, or parts thereof, i.e. immunodominant epitopes and inducers of cellular immunity, or recombinantly prepared antigens, can, nevertheless, also be used to develop and prepare vaccines.

EXAMPLE 1

(Culturing of the Virus)

The immunodeficiency virus according to the invention, MVP-2901/94, was isolated from the blood of a female patient exhibiting signs of immune deficiency. To do this, peripheral mononuclear cells (peripheral blood lymphocytes, PBL), and peripheral lymphocytes from the blood (PBL) of a donor who was not infected with HIV, were stimulated with phytohemagglutinin and maintained in culture. For this, the customary medium RPMI 1640 containing 10% fetal calf serum was used. The culture conditions are described in Landay A. et al., J. Inf. Dis. 161 (1990) pp. 706–710. No formation of giant cells was observed. The production of HI viruses was determined by measuring the p 24 antigen using the test which is commercially available from Abbott. Another test which was employed for determining the growth of the viruses was the test using particle-bound reverse transcriptase (Eberle J., Seibl R., J. Virol. Methods 40, 1992, pp. 347–356). Consequently, in order to monitor the virus production, the growth of the viruses was determined once or twice a week on the basis of the enzymic activities in the culture supernatant. New donor lymphocytes were added once a week.

Once HI virus multiplication had been established, fresh peripheral lymphocytes from the blood (PBL) of healthy donors who were not infected with HIV were infected with the supernatant from the first culture. This step was repeated, and MT2 or Jurkat cells were then infected with the supernatant. In this way, it was possible to produce the immunodeficiency virus on a permanent basis.

EXAMPLE 2

DNA Isolation and Amplification and Structural Characterization of Segments of the Genome of the HIV Isolate MVP-2901/94 (Encoding gp 41)

Genomic DNA was isolated from MVP-2901/94-infected blood lymphocytes using standard methods (Current Protocols in Molecular Biology, Wiley Interscience, 1994).

In order to characterize the regions of the genome of the MVP-2901/94 isolate, PCR (polymerase chain reaction) experiments were carried out using primer pairs from the gp 41 coat protein region. The PCR (Saiki et al., Science 239: 487–491, 1988) was carried out with the following modifications:

For the amplification of HIV-specific DNA regions, 5 µl (200 µg/ml) of genomic DNA from MVP-2901/94-infected blood lymphocytes were pipetted into a 100 µl reaction mixture (0.25 mM dNTP, 1 µM for each primer, 10 mM tris/HCl, pH 8.3, 50 mM KCl, 1.5 mM MgCl$_2$, 0.001% gelatin, 2.5 units of Taq polymerase (Perkin Elmer)) and amplified in accordance with the following temperature program: 1. initial denaturation: 3 min. 95° C., 2. amplification: 90 sec. 94° C., 60 sec. 56° C., 90 sec. 72° C. (30 cycles).

The primers which were used for the PCR and the nucleotide sequencing were synthesized in a Biosearch 8750 oligonucleotide synthesizer, and the primers exhibited the following sequences:

```
    5'                                        3'  (Seq. ID NO. 3-9)
212 AGT GCA GCA GGT AGC ACT ATG
214 TTT AGT TAT GTC AAA CCA ATT C
412 GTT CCA TTT TAC TGA TGT GTA
425 TCG GTA CGA ACC CAC TCA T
431 ACT ATA CCC CTC ATT AAT GA
438 AAC TGT CAT GGA GAA TTC TTT TA
447 AGT AGT TAC TTG TAC ACA TGG
```

Since it was not possible to amplify the isolate using primers described in the literature (Lauré, F. et al., Lancet ii, (1988) 538–541 for pol 3 and pol 4, and Ou C. Y. et al., Science 239 (1988) 295–297 for sk 38/39 and sk 68/69), a wide variety of new primers, which were derived from known sequences and which were as strongly conserved as possible, were constructed and employed in all conceivable combinations while varying the reaction conditions. Surprisingly, it emerged that the combination of the primers 212 and 412, which were derived from the sequence of the MVP-5180/91 isolate, enabled the DNA of MVP-2901/94 to be amplified, thereby providing an initial lead into the sequence of the isolate.

As a result of sequencing the first amplified sample, it was possible to design the MVP-2901/94-specific primers 425 and 431. In order further to expand the region which was now known, new primers were designed in accordance with the abovementioned criteria and employed in combination with primer 425 or primer 431. Expansion in the 3' direction was then achieved using the MVP-5180/91-derived primer 214 in combination with 425, and expansion in the 5' direction was achieved using the combinations 431/438 and 431/447, with primers 438 and 447 being derived from regions which are conserved in most HIV-1 subtypes.

The amplified DNA was fractionated using a 3% "Nusieve" agarose gel (from Biozyme), and the amplified fragment was excised and treated with an equal volume of buffer (1×TBE (0.09 M tris/borate, 0.002 M EDTA, pH 8.0)). After incubating the DNA/agarose mixture at 70° C.

for 10 minutes and subsequently extracting it with phenol, the DNA was precipitated, at −20° C. for 15', from the aqueous phase by adding 1/10 vol of 3 M NaAc, pH 5.5, and 2 vol of ethanol, and then pelleted in an Eppendorf centrifuge (13000 rpm, 4° C., 10'). The pelleted DNA was dried and taken up in water and then sequenced by the Sanger (F. Sanger, Proc. Natl. Acad. Sci., 74:5463, 1977) method after the DNA concentration had been determined photometrically at 260 nm in a Beckman spectrophotometer. Instead of sequencing with Klenow DNA polymerase, the sequencing reaction was carried out using a kit from Applied Biosystems ("Taq Dye Deoxy Terminator Cycle Sequencing", Order No.: 401150). One of the primers used for the PCR was in each case employed (1 μM in each case) as the primer in separate sequencing reactions. The sequencing reaction was analyzed in an Applied Biosystems 373A DNA sequencer in accordance with the manufacturer's instructions.

The nucleotide sequence of the amplified DNA region, and the amino acid sequence deduced from it, are depicted in Table 1 (Seq. ID No.: 10)

TABLE 1

```
      TCAGGTAATATCTTAGTGACCCTAAATTCTACTATAAACATGACCTGCGTGAGGCCAGGA
   1  ---------+---------+---------+---------+---------+---------+  60
      AGTCCATTATAGAATCACTGGGATTTAAGATGATATTTGTACTGGACGCACTCCGGTCCT

S   G   N   I   L   V   T   L   N   S   T   I   N   M   T   C   V   R   P   G

AATAATCCAGTACAGGAGATAAGGATAGGTCCAATGGCTTGGTACAGTATGGGACTTGAG
  61  ---------+---------+---------+---------+---------+---------+
      TTATTAGGTCATGTCCTCTATTCCTATCCAGGTTACCGAACCATGTCATACCCTGAACTC

N   N   P   V   Q   E   I   R   I   G   P   M   A   W   Y   S   M   G   L   E

AGAGGGTATACAAATAAATCAAGAATAGCTTATTGTGCCTATAATGTCACAAAATGGAAA
 121  ---------+---------+---------+---------+---------+---------+
      TCTCCCATATGTTTATTTAGTTCTTATCGAATAACACGGATATTACAGTGTTTTACCTTT

R   G   Y   T   N   K   S   R   I   A   Y   C   A   Y   N   V   T   K   W   K

GAAACCTTGCAAGGGATAGCTGAAAGGTATTTAGAACTTGTAAATTATTCAAGAAACATG
 181  ---------+---------+---------+---------+---------+---------+
      CTTTGGAACGTTCCCTATCGACTTTCCATAAATCTTGAACATTTAATAAGTTCTTTGTAC

E   T   L   Q   G   I   A   E   R   Y   L   E   L   V   N   Y   S   R   N   M

ACCATAACATTCAATAGCAGCATTGGTGGAGGAGATATAGAAGTAACCCGTTTGCATTTT
 241  ---------+---------+---------+---------+---------+---------+
      TGGTATTGTAAGTTATCGTCGTAACCACCTCCTCTATATCTTCATTGGGCAAACGTAAAA

T   I   T   F   N   S   S   I   G   G   G   D   I   E   V   T   R   L   H   F

AACTGTCATGGAGAATTCTTTTATTGTAACACAAGTCAAATGTTTAATTATACATTCAAA
 301  ---------+---------+---------+---------+---------+---------+
      TTGACAGTACCTCTTAAGAAAATAACATTGTGTTCAGTTTACAAATTAATATGTAAGTTT

N   C   H   G   E   F   F   Y   C   N   T   S   Q   M   F   N   Y   T   F   K

TGTAATAACTCCAAATGTAATACTCATAATGACAATAATACTTATGAGAACAGTACAAGA
 361  ---------+---------+---------+---------+---------+---------+
      ACATTATTGAGGTTTACATTATGAGTATTACTGTTATTATGAATACTCTTGTCATGTTCT

C   N   N   S   K   C   N   T   H   N   D   N   N   T   Y   E   N   S   T   R

ATAATATATTGCCAGTTGAGACAGGTAGTAAGGTCATGGATGAGGGGAGGGTCAGGGCTC
 421  ---------+---------+---------+---------+---------+---------+
      TATTATATAACGGTCAACTCTGTCCATCATTCCAGTACCTACTCCCCTCCCAGTCCCGAG

I   I   Y   C   Q   L   R   Q   V   V   R   S   W   M   R   G   G   S   G   L

TATGCACCTCCTATCAGAGGTAATCTAACCTGCAATTCAAACATAACTGGATTGATTCTA
 481  ---------+---------+---------+---------+---------+---------+
      ATACGTGGAGGATAGTCTCCATTAGATTGGACGTTAAGTTTGTATTGACCTAACTAAGAT

Y   A   P   P   I   R   G   N   L   T   C   N   S   N   I   T   G   L   I   L

CAAATGGATACACCATATAATAAAAGCTCCAACATCACATTTAGACCAATAGGAGGAGAT
```

TABLE 1-continued

```
541  ---------+---------+---------+---------+---------+---------+
     GTTTACCTATGTGGTATATTATTTTCGAGGTTGTAGTGTAAATCTGGTTATCCTCCTCTA

Q   M   D   T   P   Y   N   K   S   S   N   I   T   F   R   P   I   G   G   D

ATGAAGGATATATGGAGAACCCAAATGTACAATTACAAAGTAGTAAGGGTAAAATCTTTT
601  ---------+---------+---------+---------+---------+---------+
     TACTTCCTATATACCTCTTGGGTTTACATGTTAATGTTTCATCATTCCCATTTTAGAAAA

M   K   D   I   W   R   T   Q   M   Y   N   Y   K   V   V   R   V   K   S   F

AGTGTAGCACCTACTAAGATTAGTAGACCAGTTATAGGCACTAACCATCAAAGAGAAAAA
661  ---------+---------+---------+---------+---------+---------+
     TCACATCGTGGATGATTCTAATCATCTGGTCAATATCCGTGATTGGTAGTTTCTCTTTTT

S   V   A   P   T   K   I   S   R   P   V   I   G   T   N   H   Q   R   E   K

AGGGCAGTAGGATTGGGAATGCTATTCTTGGGGGTTCTAAGTGCAGCAGGTAGCACTATG
721  ---------+---------+---------+---------+---------+---------+
     TCCCGTCATCCTAACCCTTACGATAAGAACCCCCAAGATTCACGTCGTCCATCGTGATAC

R   A   V   G   L   G   M   L   F   L   G   V   L   S   A   A   G   S   T   M

GGCGCAGCGGGAGTAACGCTGTCGGTACGAACCCACTCATTAATGAGGGGTATAGTGCAA
781  ---------+---------+---------+---------+---------+---------+
     CCGCGTCGCCCTCATTGCGACAGCCATGCTTGGGTGAGTAATTACTCCCCATATCACGTT

G   A   A   G   V   T   L   S   V   R   T   H   S   L   M   R   G   I   V   Q

CAGCAGGACAACCTGCTGAGAGCAATACAGGCCCAGCAACATCTGCTGAGGTTATCTGTA
841  ---------+---------+---------+---------+---------+---------+
     GTCGTCCTGTTGGACGACTCTCGTTATGTCCGGGTCGTTGTAGACGACTCCAATAGACAT

Q   Q   D   N   L   L   R   A   I   Q   A   Q   Q   H   L   L   R   L   S   V

TGGGGTATTAGACAACTCCGAGCTCGCCTGCAAGCCTTAGAAACCCTTATGCAGAATCAG
901  ---------+---------+---------+---------+---------+---------+
     ACCCCATAATCTGTTGAGGCTCGAGCGGACGTTCGGAATCTTTGGGAATACGTCTTAGTC

W   G   I   R   Q   L   R   A   R   L   Q   A   L   E   T   L   M   Q   N   Q

CAACTCCTAAACCTGTGGGGCTGTAAAGGAAAATTAATCTGCTACACATCAGTAAAATGG
961  ---------+---------+---------+---------+---------+---------+
     GTTGAGGATTTGGACACCCCGACATTTCCTTTTAATTAGACGATGTGTAGTCATTTTACC

Q   L   L   N   L   W   G   C   K   G   K   L   I   C   Y   T   S   V   K   W

AACGAAACATGGGGAGGAAATCTCTCAATTTGGGACAGCTTAACATGGCA
1021 ---------+---------+---------+---------+ 1070
     TTGCTTTGTACCCCTCCTTTAGAGAGTTAAACCCTGTCGAATTGTACCGT

N   E   T   W   G   G   N   L   S   I   W   D   S   L   T   W
```

EXAMPLE 3

Distinguishing the MVP-2901/94 isolate from other HIV isolates

The nucleotide sequence which was found, and which is depicted in Table 1, was examined for homologous sequences in the GENEBANK database (Release 83, June 1994) and the EMBL database (Release 38, March 1994), while the protein sequence deduced from it was examined with the SWISSPROT protein database (Release 28, February 1994) using the GCG computer program (Genetic Computer Group, Inc. Wisconsin USA, version 7.1, March 1992). Most of the nucleotide sequences which were known in July 1994 for immunodeficiency viruses of human origin, and for isolates from primates are contained in these databases.

In the best instance, the nucleotide sequence in Table 1 exhibits an homology of 79.6% with an HIV-1 subtype O isolate. The best homology with another HIV-1 subtype is 59.6%. At best, the DNA in Table 1 is 51.6% homologous with HIV-2 isolates.

In the best instance, the amino acid sequence in Table 1 exhibits 72.7% homology with the corresponding coat protein segment of a representative of HIV-1 subtype O, and in the best instance exhibits 52.1% homology with the HIV-1 isolate HIV-1-Mal. The amino acid sequence in Table 1 is at best 37.0% homologous with HIV-2 coat proteins (HIV-2 ROD isolate).

TABLE 2

Comparisons of the homology between MVP-2901/94 and other HIV isolates at the nucleotide and protein levels

|  | Best homologies with HIV-1 subtype O representatives | Best homology with another HIV-1 subtype | Best homology with an HIV-2 isolate |
| --- | --- | --- | --- |
| Nucelotide level | 79.1% ANT70<br>78.0% MVP-5180 | 59.6% HIV1u8450 (Subtype B) | 51.6% HIV2U1GMN |
| Protein level | 72.7% ANT70<br>70.3% MVP-5180 | 52.1% HIV-1MAL (Subtype B) | 37.0% HIV-2ROD |

On the basis of the homology comparisons, the MVP-2901/94 isolate is most similar to the two isolates MVP-5180/91 and ANT70, which have provisionally been designated as HIV-1 subtype O. Nevertheless, there exists a relatively high sequence heterology, of at least 20.9% at the nucleotide level and of at least 27.3% at the protein level, with respect to the two isolates.

The present invention therefore relates to peptides which can be prepared recombinantly or synthetically and which exhibit the sequence given in Table 1, or a constituent sequence, with the constituent sequences having at least 10 consecutive amino acids, preferably 20, and particularly preferably 25, consecutive amino acids.

The present invention relates, therefore, to viruses, DNA sequences, amino acid sequences and constituent sequences thereof which exhibit an homology with the sequence depicted in Table 1 such that, based on the diagnostically relevant gene locus, at most the proportions given in Table 3, expressed in % values, are different.

TABLE 3

Homology based in gene loci, expressed as maximum differences in the protein sequence

| Gene locus | Differences | Preferred differences | Particularly preferred differences |
| --- | --- | --- | --- |
| ENV | 25% | 15% | 10% |

The ENV region is the diagnostically relevant region of the coat protein, which region is given in Table 1 both as the nucleotide sequence and as the amino acid sequence.

The homology values given in % in Table 3 mean that when the protein sequence according to Table 1 is compared with a sequence from another virus, at most a proportion of the sequence corresponding to the abovementioned percentages is allowed to be different.

EXAMPLE 4

Serological Data Relating to MVP-2901/94

In order to evaluate the importance of this virus for serodiagnosis, a serum sample from the patient infected with 2901 was examined in various commercial anti-HIV-1/2 screening tests.

The results of these investigations are presented in Table 4.

TABLE 4

| Sample | Enzygnost anti-HIV-1/-HIV-2 | Abbott Anti-HIV-1/2, 3rd generation | Ortho/CBC Anti-HIV-1/2 | 2901 gp 41 peptide |
|---|---|---|---|---|
| 2901 | 0.7 | 0.5 | 0.4 | 4.2 |

Values in O.D./cut-off ratio

It is evident from Table 4 that none of the commercially available test kits detects this sample. If, by contrast, a novel ELISA is employed which uses a peptide (NQQRLNLW- GCKGKLICYTSVKWN) which, with the exception of one amino acid (NQQRL instead of NQQLL), corresponds to the 2901 sequence as the solid phase antigen and uses the Enzygnost anti-HIV-1/2 reagents as the liquid reagents, the sample is then detected reliably. Commercially available Western blots such as, for example, that from Pasteur, do not detect this MVP2901/94 sample (not illustrated). Such Western blots would, therefore, very probably give a false negative result with samples deriving from an MVP2901/94 infection.

A particularly preferred region of the amino acid sequence depicted in Table 1 is the region which begins with the amino acid sequence NQQLL . . . (this region begins roughly at nucleotide 1010 according to the numeration used in Table 1).

Example 4 also demonstrates that, in order to exploit the disclosure of the present invention diagnostically, minor alterations may be made in the amino acid sequence without this having a detrimental effect on the diagnostic relevance of a corresponding test.

We claim:

1. An isolated virus which binds with antibodies to a polypeptide wherein said polypeptide consists of the amino acid sequence at positions 319–341 in SEQ ID NO: 12.

2. The isolated virus of claim 1, wherein said virus is a retrovirus, the genome of which consists of a nucleotide sequence which is at least 85% identical to the nucleotide sequence of the genome of retrovirus MVP 2901/94 which has been deposited with the European Collection of Animal Cell Culture (ECACC) under No. 95012601 and wherein said isolated virus has all the morphological and immunological properties of retrovirus MVP-2901/94.

3. The isolated retrovirus of claim 2, the genome of which consists of a nucleotide sequence which is at least 90% identical to the nucleotide sequence to the genome of retrovirus MVP-2901/94.

4. Isolated virus having the ECACC accession no. V 95012601.

5. An isolated polypeptide consisting of an amino acid sequence set forth in SEQ ID NO: 12.

6. An isolated virus having all the identifying characteristics of the virus designated MVP 2901/94 having ECACC Accession No. 95012601.

* * * * *

UNITED STATES PATENT AND TRADEMARK OFFICE
CERTIFICATE OF CORRECTION

PATENT NO. : 6,162,631
DATED : December 19, 2000
INVENTOR(S) : Hans-Peter Hauser Page 1 of 1

It is certified that error appears in the above-identified patent and that said Letters Patent is hereby corrected as shown below:

<u>Title page,</u>
After assignee delete "Behringwerke Aktiengesellschaft," and insert therefore -- Dade Behring Marburg GmbH --.

Signed and Sealed this

Nineteenth Day of March, 2002

*Attest:*

*Attesting Officer*

JAMES E. ROGAN
*Director of the United States Patent and Trademark Office*

```
                              SEQUENCE LISTING (1) GENERAL INFORMATION:

(iii) NUMBER OF SEQUENCES: 12

(2) INFORMATION FOR SEQ ID NO:  1:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO:   1:

AGTGCAGCAG GTAGCACTAT G                                                  21

(2) INFORMATION FOR SEQ ID NO:  2:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO:   2:

GTTCCATTTT ACTGATGTGT A                                                  21

(2) INFORMATION FOR SEQ ID NO:  3:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO:   3:

AGTGCAGCAG GTAGCACTAT G                                                  21

(2) INFORMATION FOR SEQ ID NO:  4:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO:   4:
```

```
TTTAGTTATG TCAAACCAAT TC                                             22

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 5:

GTTCCATTTT ACTGATGTGT A                                              21

(2) INFORMATION FOR SEQ ID NO: 6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 6:

TCGGTACGAA CCCACTCAT                                                 19

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 7:

ACTATACCCC TCATTAATGA                                                20

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 8:

AACTGTCATG GAGAATTCTT TTA                                            23

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 9:

AGTAGTTACT TGTACACATG G                                              21
```

(2) INFORMATION FOR SEQ ID NO: 10:

(i) SEQUENCE CHARACTERISTICS:
        (A) LENGTH: 1070 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 10:

```
TCAGGTAATA TCTTAGTGAC CCTAAATTCT ACTATAAACA TGACCTGCGT GAGGCCAGGA    60

AATAATCCAG TACAGGAGAT AAGGATAGGT CCAATGGCTT GGTACAGTAT GGGACTTGAG   120

AGAGGGTATA CAAATAAATC AAGAATAGCT TATTGTGCCT ATAATGTCAC AAAATGGAAA   180

GAAACCTTGC AAGGGATAGC TGAAAGGTAT TTAGAACTTG TAAATTATTC AAGAAACATG   240

ACCATAACAT TCAATAGCAG CATTGGTGGA GGAGATATAG AAGTAACCCG TTTGCATTTT   300

AACTGTCATG GAGAATTCTT TTATTGTAAC ACAAGTCAAA TGTTTAATTA TACATTCAAA   360

TGTAATAACT CCAAATGTAA TACTCATAAT GACAATAATA CTTATGAGAA CAGTACAAGA   420

ATAATATATT GCCAGTTGAG ACAGGTAGTA AGGTCATGGA TGAGGGGAGG GTCAGGGCTC   480

TATGCACCTC CTATCAGAGG TAATCTAACC TGCAATTCAA ACATAACTGG ATTGATTCTA   540

CAAATGGATA CACCATATAA TAAAAGCTCC AACATCACAT TTAGACCAAT AGGAGGAGAT   600

ATGAAGGATA TATGGAGAAC CCAAATGTAC AATTACAAAG TAGTAAGGGT AAAATCTTTT   660

AGTGTAGCAC CTACTAAGAT TAGTAGACCA GTTATAGGCA CTAACCATCA AAGAGAAAAA   720

AGGGCAGTAG GATTGGGAAT GCTATTCTTG GGGGTTCTAA GTGCAGCAGG TAGCACTATG   780

GGCGCAGCGG GAGTAACGCT GTCGGTACGA ACCCACTCAT TAATGAGGGG TATAGTGCAA   840

CAGCAGGACA ACCTGCTGAG AGCAATACAG GCCCAGCAAC ATCTGCTGAG GTTATCTGTA   900

TGGGGTATTA GACAACTCCG AGCTCGCCTG CAAGCCTTAG AAACCCTTAT GCAGAATCAG   960

CAACTCCTAA ACCTGTGGGG CTGTAAAGGA AAATTAATCT GCTACACATC AGTAAAATGG  1020

AACGAAACAT GGGGAGGAAA TCTCTCAATT TGGGACAGCT AACATGGCA              1070
```

(2) INFORMATION FOR SEQ ID NO: 11:

(i) SEQUENCE CHARACTERISTICS:
        (A) LENGTH: 1070 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 11:

```
AGTCCATTAT AGAATCACTG GGATTTAAGA TGATATTTGT ACTGGACGCA CTCCGGTCCT    60

TTATTAGGTC ATGTCCTCTA TTCCTATCCA GGTTACCGAA CCATGTCATA CCCTGAACTC   120

TCTCCCATAT GTTTATTTAG TTCTTATCGA ATAACACGGA TATTACAGTG TTTTACCTTT   180

CTTTGGAACG TTCCCTATCG ACTTTCCATA AATCTTGAAC ATTTAATAAG TTCTTTGTAC   240

TGGTATTGTA AGTTATCGTC GTAACCACCT CCTCTATATC TTCATTGGGC AAACGTAAAA   300

TTGACAGTAC CTCTTAAGAA AATAACATTG TGTTCAGTTT ACAAATTAAT ATGTAAGTTT   360

ACATTATTGA GGTTTACATT ATGAGTATTA CTGTTATTAT GAATACTCTT GTCATGTTCT   420

TATTATATAA CGGTCAACTC TGTCCATCAT TCCAGTACCT ACTCCCCTCC CAGTCCCGAG   480

ATACGTGGAG GATAGTCTCC ATTAGATTGG ACGTTAAGTT TGTATTGACC TAACTAAGAT   540
```

```
GTTTACCTAT GTGGTATATT ATTTTCGAGG TTGTAGTGTA AATCTGGTTA TCCTCCTCTA    600

TACTTCCTAT ATACCTCTTG GGTTTACATG TTAATGTTTC ATCATTCCCA TTTTAGAAAA    660

TCACATCGTG GATGATTCTA ATCATCTGGT CAATATCCGT GATTGGTAGT TTCTCTTTTT    720

TCCCGTCATC CTAACCCTTA CGATAAGAAC CCCCAAGATT CACGTCGTCC ATCGTGATAC    780

CCGCGTCGCC CTCATTGCGA CAGCCATGCT TGGGTGAGTA ATTACTCCCC ATATCACGTT    840

GTCGTCCTGT TGGACGACTC TCGTTATGTC CGGGTCGTTG TAGACGACTC CAATAGACAT    900

ACCCCATAAT CTGTTGAGGC TCGAGCGGAC GTTCGGAATC TTTGGGAATA CGTCTTAGTC    960

GTTGAGGATT TGGACACCCC GACATTTCCT TTTAATTAGA CGATGTGTAG TCATTTTACC   1020

TTGCTTTGTA CCCCTCCTTT AGAGAGTTAA ACCCTGTCGA ATTGTACCGT              1070
```

(2) INFORMATION FOR SEQ ID NO: 12:

(i) SEQUENCE CHARACTERISTICS:
        (A) LENGTH: 356 amino acids
        (B) TYPE: amino acid
        (C) STRANDEDNESS: unknown
        (D) TOPOLOGY: unknown (ii) MOLECULE TYPE: Protein (v) FRAGMENT TYPE: internal (xi) SEQUENCE DESCRIPTION: SEQ ID NO: 12:

```
Ser Gly Asn Ile Leu Val Thr Leu Asn Ser Thr Ile Asn Met Thr Cys
 1               5                  10                  15

Val Arg Pro Gly Asn Asn Pro Val Gln Glu Ile Arg Ile Gly Pro Met
                20                  25                  30

Ala Trp Tyr Ser Met Gly Leu Glu Arg Gly Tyr Thr Asn Lys Ser Arg
            35                  40                  45

Ile Ala Tyr Cys Ala Tyr Asn Val Thr Lys Trp Lys Glu Thr Leu Gln
        50                  55                  60

Gly Ile Ala Glu Arg Tyr Leu Glu Leu Val Asn Tyr Ser Arg Asn Met
 65                  70                  75                  80

Thr Ile Thr Phe Asn Ser Ser Ile Gly Gly Gly Asp Ile Glu Val Thr
                85                  90                  95

Arg Leu His Phe Asn Cys His Gly Glu Phe Phe Tyr Cys Asn Thr Ser
            100                 105                 110

Gln Met Phe Asn Tyr Thr Phe Lys Cys Asn Asn Ser Lys Cys Asn Thr
        115                 120                 125

His Asn Asp Asn Asn Thr Tyr Glu Asn Ser Thr Arg Ile Ile Tyr Cys
    130                 135                 140

Gln Leu Arg Gln Val Val Arg Ser Trp Met Arg Gly Gly Ser Gly Leu
145                 150                 155                 160

Tyr Ala Pro Pro Ile Arg Gly Asn Leu Thr Cys Asn Ser Asn Ile Thr
                165                 170                 175

Gly Leu Ile Leu Gln Met Asp Thr Pro Tyr Asn Lys Ser Ser Asn Ile
            180                 185                 190

Thr Phe Arg Pro Ile Gly Gly Asp Met Lys Asp Ile Trp Arg Thr Gln
        195                 200                 205

Met Tyr Asn Tyr Lys Val Val Arg Val Lys Ser Phe Ser Val Ala Pro
    210                 215                 220

Thr Lys Ile Ser Arg Pro Val Ile Gly Thr Asn His Gln Arg Glu Lys
225                 230                 235                 240

Arg Ala Val Gly Leu Gly Met Leu Phe Leu Gly Val Leu Ser Ala Ala
```

-continued

```
                    245                 250                 255
Gly Ser Thr Met Gly Ala Ala Gly Val Thr Leu Ser Val Arg Thr His
            260                 265                 270

Ser Leu Met Arg Gly Ile Val Gln Gln Gln Asp Asn Leu Leu Arg Ala
            275                 280                 285

Ile Gln Ala Gln Gln His Leu Leu Arg Leu Ser Val Trp Gly Ile Arg
        290                 295                 300

Gln Leu Arg Ala Arg Leu Gln Ala Leu Glu Thr Leu Met Gln Asn Gln
305                 310                 315                 320

Gln Leu Leu Asn Leu Trp Gly Cys Lys Gly Lys Leu Ile Cys Tyr Thr
                325                 330                 335

Ser Val Lys Trp Asn Glu Thr Trp Gly Gly Asn Leu Ser Ile Trp Asp
            340                 345                 350

Ser Leu Thr Trp
        355
```